April 19, 1938. A. F. J. BAUR Plant Pat. 273
CARNATION
Filed July 2, 1937
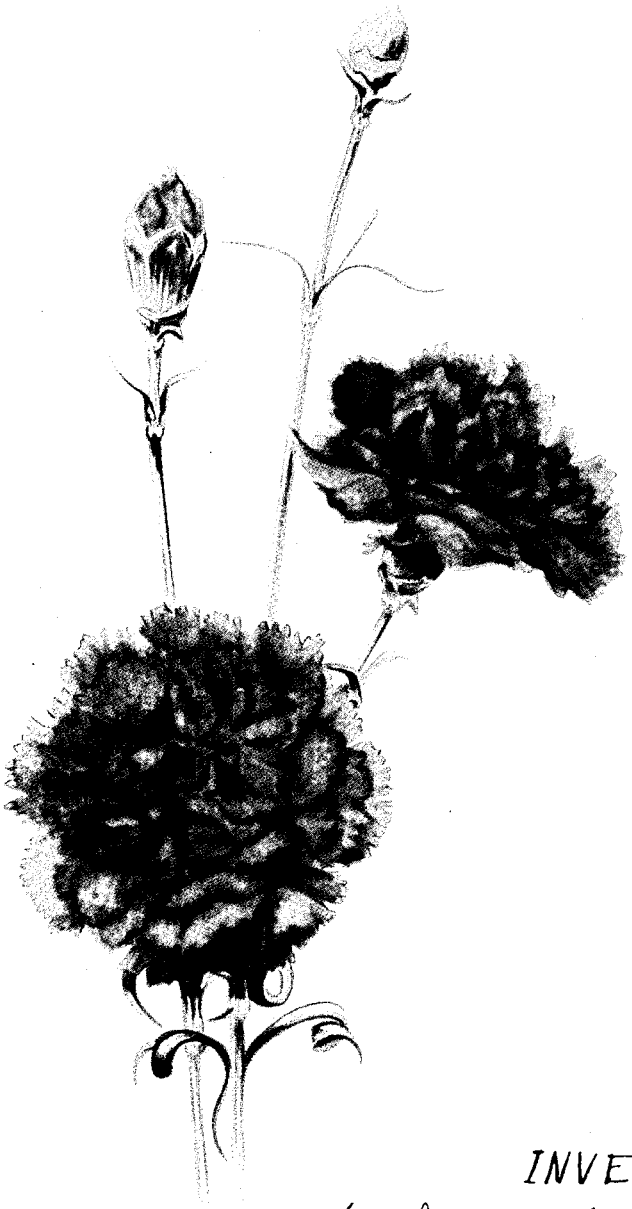
INVENTOR
Adolphe Frederick Jacob Baur
By Orville M Kile
Plant Patent Agent Patented Apr. 19, 1938

Plant Pat. 273

UNITED STATES PATENT OFFICE

273

CARNATION

Adolphe Frederick Jacob Baur, Indianapolis, Ind., assignor to Baur-Steinkamp and Company, Incorporated, Indianapolis, Ind.

Application July 2, 1937, Serial No. 151,756

1 Claim. (Cl. 47—60)

My present invention relates to carnations of the greenhouse forcing type and pertains particularly to an improvement in carnations of the dark maroon or purple class.

This new variety is a seedling resulting from a cross between the varieties Woburn and Seedling variety #15323, an undisseminated seedling developed by me. This new variety has been asexually reproduced over a period of five years and its characteristics have persisted without change.

The known variety which this new variety most nearly resembles is the Potentate. But it differs from that variety in many respects, the principal differences being as follows. Its color resembles that of Potentate but the present variety takes on its rich purple shade earlier in the development of the flower, this being a distinct advantage. The individual blossom is much larger than that of Potentate. Better and stronger plants are produced than can be produced by Potentate and they are more grassy, thus enabling the present variety to better withstand the summer heat. Although the flower is very full-petaled, the calyx seldom splits. This is a very excellent quality for a full-petaled carnation.

The accompanying illustrations show in approximately natural color and size in the original, a side view and a front view of the blossoms, a tight bud, and an opening bud, together with stems and a little of the foliage.

Following is a more detailed description of this new carnation variety. All color plate references are to Ridgway's Color Standards and Nomenclature.

*The plant*

*Growth.*—Upright and vigorous; attains a height of thirty to thirty-six inches in midwinter.

*Foliage.*—Rather grassy. Leaves moderate length and curling. Color Antique Green (Plate VI).

*Stems.*—Long, stiff, usually straight but sometimes inclined to have staggered nodes. Although the stem is not heavy, it is very strong and adequate to support the large blossom. Color Antique Green (Plate VI), covered with gray bloom.

*The flower*

*Size.*—Large and full-petaled. Averages 3¼ inches across. Center well filled.

*Color.*—There is no color in Ridgway's Color Standards and Nomenclature which describes this carnation. The nearest to the general effect is Pansy Purple (Plate XII) but this plate shows less life and brilliance than is characteristic of the new carnation variety. The outer petals are close to Amarinth Purple (Plate XII) in color. The inner petals are a little darker than this shade, some being Pansy Purple (Plate XII). As the light falls on the thickly clustered petals, shadows are formed which make the color of the flower as a whole appear darker than the individual petals. The central portion sometimes looks as dark as Violet Carmine (Plate XII), due to the shadows. A velvety quality of the petals which cannot be shown by the artist tends to give a darker effect. The lower portion of each petal, largely enclosed in the calyx, is clear white.

*Petalage.*—Average number of petals is 75, including about a dozen very small ones. For an eighth of an inch or more at the base of the petals they are attached to the outside of a sort of core upon which rests the ovary.

*Petals.*—Two and one-half inches long (one-half of length inclosed within calyx). A small portion of the white of the petals shows above the calyx. Shallow serrations on edges.

*Calyx.*—Consists of a single tube 1¼ inches long and divided into five lobes. Absinthe Green to Light Cress Green (Plate XXXI). Seldom splits.

*Reproductive organs*

*Pistils.*—To or three, one or more usually visible in the open flower. One and one-half inches or more in length. Curled at top. Purple. Arise from top of ovary.

*Stamens.*—Varying in length but most of them 1¼ to 1½ inches long. Attached to base of ovary so none extend as high as the pistils although of the same length. The longer ones are tinted lavender at the top but all are white at the base. Only a few have anthers.

*Ovary.*—Nearly ⅜ inch long. Set upon a pithy base which is about ¼ inch high. Many ovules.

Having thus disclosed my invention, I claim:

The new variety of carnation substantially as shown and described, characterized particularly by its strong and vigorous growth, its strong calyx, and its large blossom of distinctive color which color is assumed early in the flower's development.

ADOLPHE FREDERICK JACOB BAUR.